US00PP09096P

United States Patent [19]

Hefner

[11] Patent Number: Plant 9,096

[45] Date of Patent: Apr. 4, 1995

[54] HYBRID TEA ROSE PLANT NAMED CLASSIC TOUCH

[75] Inventor: John Hefner, Indianapolis, Ind.

[73] Assignee: Certified Roses, Inc., Tyler, Tex.

[21] Appl. No.: 138,033

[22] Filed: Oct. 15, 1993

[51] Int. Cl.[6] ..... A01H 5/00
[52] U.S. Cl. ..... Plt./18
[58] Field of Search ..... Plt. 18, 26, 19, 27

[56] References Cited

PUBLICATIONS

Modern Roses 9 1986, Compiled by the American Rose Society, Shreveport, La., p. 341.

*Primary Examiner*—Howard J. Locker
*Attorney, Agent, or Firm*—Christie, Parker & Hale

[57] ABSTRACT

A new hybrid tea rose plant producing light pink flowers.

1 Drawing Sheet

SUMMARY OF THE INVENTION

The present invention relates to a new and distinct variety of rose plant of the hybrid tea rose class which is a sport of the variety known as 'Touch of Class' U.S. Plant Pat. No. 5,165, the disclosure of which is expressly incorporated herein by reference. The varietal denomination of this new rose is 'Classic Touch'.

The new variety is a natural mutation of 'Touch of Class', also known as 'Kricarlo'. The parent is described in Modern Roses 10 as producing flowers which are medium pink shaded with coral and cream. Nominally, the flowers of Touch of Class have about 33 petals. In contrast, the new variety produces flowers which are near white to very light pink 26 to 40 petals. The reproductive organs, including the stamens and styles, are similar to 'Kricarlo', as are the hips, petioles, leaves, new wood, thorns and prickles.

Among the novel characteristics possessed by this new variety which distinguish it from its parent and all other varieties of which I am aware are its attractive lighter pink flower borne on a more vigorous plant.

Asexual reproduction by budding of the new variety as performed in Smith County, Tex. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DETAILED DESCRIPTION OF THE NEW VARIETY

Parentage: Sport of 'Touch of Class'.
Class: Hybrid Tea.

The following is a detailed description of my new variety, of specimens grown outdoors in Watsonville, Calif. in the month of June. The color terminology used as in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:
- (1) *Size.*—Medium.
- (2) *Form.*—Pointed.
- (3) *Color.*—When sepals first divide, bud color is near 36° C.
- (4) *Sepals.*—Long, slender, light green, near 144A on outside; near 148C at edges with near 144D in center on inside.
- (5) *Peduncle.*—Length: Average. Aspect: Straight. Strength: Erect. Color: Near 147C.

B. Bloom:
- (1) Size.—Average size when fully expanded—about 3½ to 4 inches.
- (2) *Borne.*—Singly, one to a stem and sometimes in sprays of 3 blooms.
- (3) *Form.*—High centered, slight recurve at maturity.
- (4) *Petalage.*—Number of petals under normal conditions — about 30–35.
- (5) *Color.*—⅓ to ½ open: top surface of outer petals is near 56D to 56C undersurface of outer petals is near 36C; top surface of inner petals is near 36D; undersurface of inner petals is near 36D; base of petals at point of attachment is near 29D and the general tonality from a distance is near 56D to 56C. Fully open blooms: top surface of outer petals is near 49D; undersurface of outer petals is near 49C; top surface of inner petals is near 36D; undersurface of inner petals is near 36C; base of petals at point of attachment is near 155A and the general tonality from a distance is near 36D. Color of bloom upon aging lightens to a pale pink with the petal top surface changing to near 36D and the petal undersurface to near 36D.

C. Petals:
- (1) *Texture.*—Average.
- (2) *Appearance.*—Inside satiny; outside satiny.
- (3) *Form.*—Broadfan shape.
- (4) *Arrangement.*—Imbricated.
- (5) *Petaloids.*—Many.
- (6) *Fragrance.*—Slight to none.
- (7) *Lasting quality.*—Similar to parent 'Kricarlo'.
- (8) *Persistence.*—Drop off cleanly.

REPRODUCTIVE ORGANS

A. Stamens:
(1) *Arrangement.*—Regularly arranged.
(2) *Pollen.*—Color — near 11C.

B. Pistils
(1) *Styles.*—Uneven, medium length.
(2) *Stigmas.*—Color — near 50B.

C. Characteristics of Hips: Globular, average size. orange at maturity, seeds protrude slightly.

PLANT

A. Form: Upright.

B. Growth: Very vigorous; height attained about 5 feet at first season.

C. Foliage: Compound 3 to 5 leaflets.
(1) *Size.*—Medium to large slightly longer than parent 'Kricarlo'.
(2) *Quantity.*—Abundant.
(3) *Color.*—New foliage: Upper side — near 183B. Underside — near 143B. Old foliage: Upper side — near 143A. Underside — near 143B.
(4) *Shape.*—Elliptic.
(5) *Texture.*—Leathery.
(6) *Edge.*—Serrated.
(7) *Serration.*—Denticulate.
(8) *Leaf stem.*—Color — medium green.
(9) *Stipules.*—Medium.
(10) *Petioles.*—Purplish.
(11) *Auricle.*—Long, pointed.
(12) *Resistance to disease.*—Average to blackspot; average to mildew; average to rust.

D. Wood
(1) *New wood.*—Color — new shoots light green. Bark — smooth.
(2) *Old wood.*—Color — medium green. Bark — smooth.

E. Flower stem: About 10 inches from last cut.

F. Thorns:
*Quantity (main stalk).*—Ordinary.
*On laterals from stalk.*—Average.
*Form.*—Slightly curved downward.
*Length.*—Medium.
*Color.*—Light green to cream.
*Position.*—Irregular.
*Prickles.*—Some.

F. Winter hardiness: Needs protection in winter climates.

I claim:

1. A new and distinct variety of rose plant of the hybrid tea rose class, substantially as shown and described.

* * * * *

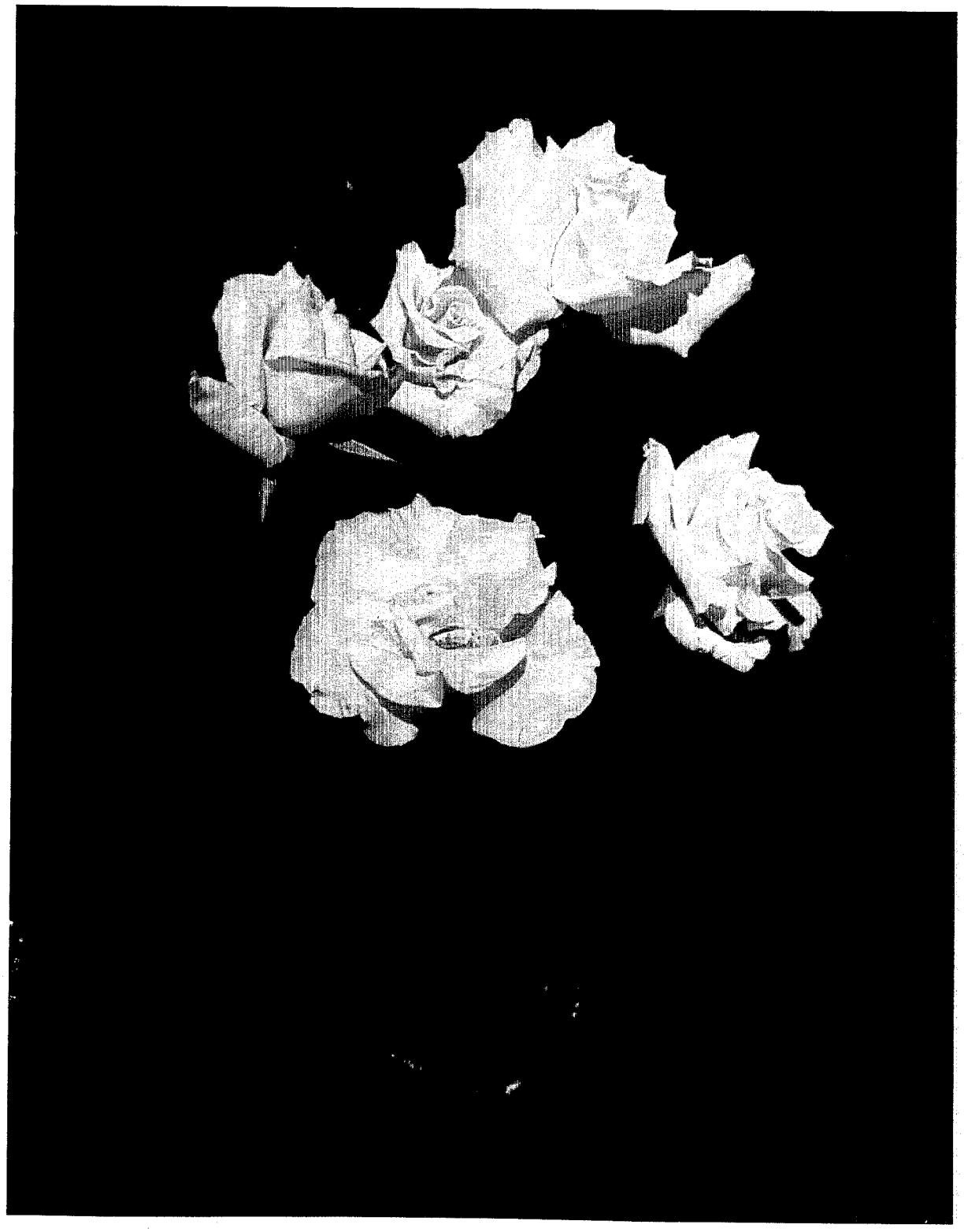

UNITED STATES PATENT AND TRADEMARK OFFICE

CERTIFICATE OF CORRECTION

PATENT NO. : Plant 9,096

DATED : April 4, 1995

INVENTOR(S) : John Hefner

It is certified that error appears in the above-indentified patent and that said Letters Patent is hereby corrected as shown below:

On the Title Page, Item 56, References Cited, under "References Cited" insert
-- U.S. PATENT DOCUMENTS
PP7509 4/1991 Kordes....PLT/18
PP5165 12/1983 Kriloff...PLT/18 --.

Column 1, line 22, change "pink flower" to -- pink flowers --.

Column 1, line 44, before "in accordance" change "as" to -- is --.

Column 2, line 8, change "36°C" to -- 36C --.

Signed and Sealed this

Twelfth Day of September, 1995

*Attest:*

*Attesting Officer*

BRUCE LEHMAN

*Commissioner of Patents and Trademarks*